(12) United States Patent
Phillips

(10) Patent No.: US 11,494,474 B2
(45) Date of Patent: Nov. 8, 2022

(54) BRAIN ACTIVITY-BASED AUTHENTICATION

(71) Applicant: MASTERCARD INTERNATIONAL INCORPORATED, Purchase, NY (US)

(72) Inventor: Simon Phillips, York (GB)

(73) Assignee: MASTERCARD INTERNATIONAL INCORPORATED, Purchase, NY (US)

( * ) Notice: Subject to any disclaimer, the term of this patent is extended or adjusted under 35 U.S.C. 154(b) by 228 days.

(21) Appl. No.: 16/676,082

(22) Filed: Nov. 6, 2019

(65) Prior Publication Data
US 2020/0151308 A1 May 14, 2020

(30) Foreign Application Priority Data
Nov. 12, 2018 (EP) .................... 18205785

(51) Int. Cl.
*G06F 21/32* (2013.01)
*G06F 21/36* (2013.01)
(Continued)

(52) U.S. Cl.
CPC .............. *G06F 21/32* (2013.01); *A61B 5/246* (2021.01); *A61B 5/377* (2021.01); *G06F 21/36* (2013.01);
(Continued)

(58) Field of Classification Search
CPC .......... G06F 21/32; G06F 21/36; G06F 21/40; A61B 5/246; A61B 5/377; G06K 9/00885;
(Continued)

(56) References Cited

U.S. PATENT DOCUMENTS 9,058,473 B2  6/2015 Navratil et al.
2007/0060831 A1  3/2007 Le et al.
(Continued)

FOREIGN PATENT DOCUMENTS

EP   2722001 A1   4/2014
EP   3160106 A1   4/2017
WO   WO2015/017563   2/2015

OTHER PUBLICATIONS https://arxiv.org/ftp/arxiv/papers/1612/1612.09423.pdf ("Svogor") (Year: 2016).*

(Continued)

*Primary Examiner* — Florian M Zeender
*Assistant Examiner* — Joseph M Mutschler
(74) *Attorney, Agent, or Firm* — Harness, Dickey & Pierce, P.L.C.

(57) ABSTRACT

A method of authentication of a user is provided. The method comprises capturing a brain activity signal from a user; comparing the brain activity signal with reference data; and determining, based at least in part on the comparison, whether the identity of the user can be confirmed. Also provided is a computing device comprising at least one processor and at least one memory. The computing device is adapted to: communicate with a brain activity sensing system to capture a brain activity signal from the user; provide the captured brain activity signal to an authentication service computing system; and authenticate the user based at least in part on the result of a comparison with reference data received from the authentication service computing system. A system comprising the computing device and a brain activity sensing system, and am authentication service computing device are also provided.

9 Claims, 7 Drawing Sheets

(51) Int. Cl.
  *G06F 21/40* (2013.01)
  *G06Q 20/10* (2012.01)
  *G06Q 20/20* (2012.01)
  *G06Q 20/40* (2012.01)
  *A61B 5/246* (2021.01)
  *A61B 5/377* (2021.01)
  *G06V 40/10* (2022.01)
  *G06Q 20/32* (2012.01)

(52) U.S. Cl.
  CPC ......... *G06F 21/40* (2013.01); *G06Q 20/1085* (2013.01); *G06Q 20/20* (2013.01); *G06Q 20/32* (2013.01); *G06Q 20/4012* (2013.01); *G06Q 20/40145* (2013.01); *G06V 40/10* (2022.01); *G06V 40/15* (2022.01)

(58) Field of Classification Search
  CPC ..... G06K 2009/00939; G06Q 20/1085; G06Q 20/20; G06Q 20/4012; G06Q 20/40145
  See application file for complete search history.

(56) References Cited

U.S. PATENT DOCUMENTS

| 2008/0177197 | A1  | 7/2008 | Lee et al. |
| 2016/0103487 | A1* | 4/2016 | Crawford ............... A61B 5/117 600/544 |
| 2018/0012009 | A1* | 1/2018 | Furman .................... G06N 3/08 |
| 2018/0169411 | A1* | 6/2018 | Goodall ............. A61N 1/37247 |

OTHER PUBLICATIONS

"Pass-thoughts: Authenticating With Our Minds", Julie Thorpe et al., International Association for Cryptologic Research, Apr. 22, 2005, 1-14 pgs.

"Electroencephalogram subject identification: A review", Del Pozo-Banos Marcos et al., Expert Systems With Applications, vol. 41, No. 15, May 22, 2014, pp. 6537-6554.

\* cited by examiner

BRAIN ACTIVITY-BASED AUTHENTICATION

CROSS-REFERENCE TO RELATED APPLICATION

This application claims the benefit of, and priority to, European Patent Application No. 18205785.1 filed on Nov. 12, 2018. The entire disclosure of the above application is incorporated herein by reference.

FIELD

The present disclosure relates to improvements in authentication methods and systems and particularly, but not exclusively, in the use of brain activity measurements as a means of authentication. Aspects of the disclosure relate to a method, a computing device and a service computing system.

BACKGROUND

This section provides background information related to the present disclosure which is not necessarily prior art.

Authentication is a process in which the credentials provided by a user are examined in order to confirm the identity of the user. This is usually done by comparing submitted credential values with stored credential values, typically stored in a database protected against subversion. If the submitted user credentials match those in the database, then the user is authenticated, which generally leads to a further result, such as a grant of access to a system. This type of authentication is relevant to many fields, as it authorizes human-to-machine interactions to enable access to systems, applications, and even resources. One field in which authentication is widely used is in transaction systems, such as for making mobile payments.

Typically, authentication is carried out through the use of usernames and PINs (personal identification numbers) or passwords. Currently, password-based authentication is not considered to provide a high enough level of security in itself for many systems that contain sensitive information. Indeed, passwords and PINs can be intercepted, stolen or even guessed, sometimes without the user being aware of this. In addition, users are prone to forgetting passwords or mistakenly entering the incorrect password resulting in the system becoming locked.

Other authentication mechanisms are increasingly used. One such approach is biometric authentication. Biometric authentication uses the unique biological characteristics of individuals to validate the identity of the individual for access to a system. Examples of biological characteristics that can be relied upon for biometric authentication include fingerprints, hand geometry, retina and iris patterns, face recognition, voice waves and signatures. A biometric authentication process can be used to secure a range of electronic communications, such as online banking, logging into a computer or smartphone, or making payments. Typically, the biometric authentication system compares the captured biometric data to authentic data that is stored in a database. Provided the two data samples match with each other, authentication would be confirmed and access to the system would be granted.

There are currently many issues with biometric authentication systems. For example, systems relying on image recognition, retina scanning or a fingerprint can still be corrupted by acquisition of an image of a user's face, eye, finger or any other relevant visually identifiable biometric, or by interception of the relevant data in a previous identification process. Further, users can be coerced to provide access to a system.

Therefore, there is still a need for new authentication systems that can replace or be combined with existing authentication systems to increase the reliability and ease of use of the authentication system.

SUMMARY

This section provides a general summary of the disclosure, and is not a comprehensive disclosure of its full scope or all of its features. Aspects and embodiments of the disclosure are set out in the accompanying claims.

According to an aspect of the present disclosure there is provided a method of authentication of a user. The method comprises capturing a brain activity signal from a user. The method further comprises comparing the brain activity signal with reference data, and determining, based on the comparison, whether the identity of the user can be confirmed.

In embodiments, capturing a brain activity signal from a user comprises exposing the user to a stimulus and capturing the brain activity signal during or shortly after exposing the user to the stimulus. The stimulus may comprise a sensory stimulus. For example, the stimulus may comprise a visual stimulus, an audio stimulus, a haptic stimulus, an olfactory stimulus, or any combinations thereof. Examples of visual stimuli that may be suitable for the present disclosure include: one or more images, one or more videos, and one or more spatial or temporal patterns of light.

In some embodiments, the stimulus comprises a rapid succession of sensory stimuli.

In embodiments, comparing the brain activity signal with reference data comprises comparing the brain activity signal in response to the stimulus to reference data comprising expected brain activity signals in response to the stimulus. For example, expected brain activity signals may be obtained based on a learning data set and/or based on one or more models of brain activity.

In embodiments, capturing a brain activity signal from a user comprises requesting the user to perform an action and capturing the brain activity signal while the user is performing the action, or shortly thereafter. In some such embodiments, requesting the user to perform an action comprises requesting the user to enter a PIN, password or other secret identifier, or to select images displayed on a screen.

In embodiments where capturing a brain activity signal from a user comprises requesting the user to perform an action and capturing the brain activity signal while the user is performing the action or shortly thereafter, comparing the brain activity signal with reference data comprises comparing (i) the captured brain activity signal to (ii) reference data comprising expected brain activity signals associated with an authentic user performing the requested action.

In embodiments, requesting the user to perform an action comprises requesting the user to enter a secret identifier, and comparing the captured brain activity signal with reference data comprises comparing the captured brain activity signal to reference data comprising (i) expected brain activity signals associated with users entering secret information that they enter routinely and (ii) expected brain activity signals associated with users entering secret information that they do not enter routinely.

In embodiments, requesting the user to perform an action comprises requesting the user to select images displayed on a screen, and comparing the captured brain activity signal with reference data comprises comparing the captured brain activity signal to reference data comprising expected brain activity signals associated with the user when selecting those particular images.

In embodiments, the reference data is selected from: data uniquely associated with the user, data associated with a cohort of individuals, theoretical data, and combinations thereof.

In embodiments, capturing a brain activity signal from a user comprises requesting the user to think a predetermined thought and capturing the brain activity signal while the user is thinking the particular thought. In some such embodiments, the method may further comprise requesting the user to indicate that (s)he is thinking the particular thought and capturing the brain activity signal comprises capturing the brain activity signal when the user indicates that (s)he is thinking the particular thought.

In embodiments, the brain activity signal is an electroencephalograph or a magnetoencephalograph.

In embodiments, the brain activity signal comprises measurements of the electrical potential at one or more locations on a user's scalp. In embodiments, the measurement locations positioned according to the International 10/20 system.

In embodiments, the method comprises capturing a PIN, password or other secret identifier (for example by requesting the user to provide a PIN, password or other secret identifier), and determining whether the identity of the user can be confirmed comprises authenticating the PIN, password or secret identifier.

In embodiments, the method further comprises capturing additional biometric data associated with the user. In some such embodiments, determining whether the identity of the user can be confirmed comprises authenticating the biometric data. For example, additional biometric data may comprise fingerprint data, iris scan data, facial recognition data, etc.

In embodiments, the method further comprises processing the brain activity signal prior to comparison with the reference data. For example, the data (brain activity signal and/or reference data) may be normalized, standardized, averaged, its dimensionality reduced, etc., or combinations thereof.

According to a further aspect of the disclosure there is provided a computing device adapted for authentication of a user, comprising at least one processor and at least one memory. The computing device is adapted to: communicate with a brain activity sensing system to capture a brain activity signal from the user; provide the captured brain activity signal to an authentication service computing device for comparison with reference data; and authenticate the user based at least in part on the result of the comparison step received from the authentication service computing system.

In embodiments, the computing device is further adapted to expose the user to a stimulus and to communicate with a brain activity sensing system to capture the brain activity signal during or shortly after exposing the user to the stimulus. The stimulus may comprise a sensory stimulus, and the computing device may be adapted to generate a sensory stimulus. For example, the stimulus may comprise a visual stimulus, an audio stimulus, a haptic stimulus, an olfactory stimulus, or any combinations thereof. Examples of visual stimuli that may be suitable for the present disclosure include: one or more images, one or more videos, and one or more spatial or temporal patterns of light. In some embodiments, the stimulus comprises a rapid succession of sensory stimuli.

In some embodiments, the computing device is adapted to provide the captured brain activity signal in response to a stimulus to an authentication service computing device and authenticate the user based on the result of the comparison between (1) the brain activity signal in response to the stimulus to (2) reference data comprising expected brain activity signals in response to the stimulus.

In embodiments, the computing device is further adapted to request the user to perform an action and to communicate with a brain activity sensing system to capture the brain activity signal while the user is performing the action, or shortly thereafter. In some such embodiments, the computing device is adapted to request the user to enter a PIN, password or other secret identifier, or to select images displayed on a screen, and to record the result of the user's input.

In some embodiments, the computing device is adapted to: request the user to perform an action; communicate with a brain activity sensing system to capture the brain activity signal while the user is performing the action or shortly thereafter; provide the captured brain activity signal to an authentication service computing device; and authenticate the user based on the result of the comparison between (i) the captured brain activity signal to (ii) reference data comprising expected brain activity signals associated with an authentic user performing the requested action.

In embodiments, the computing device is adapted to: request the user to enter a secret identifier; communicate with a brain activity sensing system to capture the brain activity signal while the user is entering the secret identifier, or shortly thereafter; provide the captured brain activity signal to an authentication service computing device; and authenticate the user based on the result of the comparison between (i) the captured brain activity signal to (ii) reference data comprising expected brain activity signals associated with users entering secret information that they enter routinely and expected brain activity signals associated with users entering secret information that they do not enter routinely.

In embodiments, the computing device is adapted to: request the user to select images displayed on a screen; communicate with a brain activity sensing system to capture the brain activity signal while the user is selecting images, or shortly thereafter; provide the captured brain activity signal to an authentication service computing device; and authenticate the user based on the result of the comparison between the captured brain activity signal and reference data comprising expected brain activity signals associated with the user when selecting those particular images.

In embodiments, the reference data is selected from: data uniquely associated with the user, data associated with a cohort of individuals, theoretical data, and combinations thereof.

In embodiments, the computing device is adapted to: request the user to think a predetermined thought; and communicate with a brain activity sensing system to capture the brain activity signal while the user is thinking the particular thought. In some such embodiments, the computing device may further be adapted to request the user to indicate that (s)he is thinking the particular thought; and communicate with a brain activity sensing system to capture the brain activity signal when the user indicates that (s)he is thinking the particular thought.

In embodiments, the brain activity signal is an electroencephalograph or a magnetoencephalograph.

In embodiments, the brain activity signal comprises measurements of the electrical potential at one or more locations on a user's scalp. In embodiments, the measurement locations are positioned according to the International 10/20 system.

In embodiments, the computing device is adapted to: capturing a PIN, password or other secret identifier (for example by requesting the user to provide a PIN, password or other secret identifier); authenticate the PIN, password or secret identifier; and authenticate the user based at least in part on the result of the comparison step received from the authentication service computing system and the result of authentication of the PIN, password or secret identifier.

In embodiments, the computing device is further adapted to: capture additional biometric data associated with the user. For example, the computing device may be adapted to communicate with a scanner, camera or other data acquisition means to capture biometric data associated with the user. In some such embodiments, the computing device is adapted to authenticate the biometric data; and authenticate the user based at least in part on the result of the comparison step received from the authentication service computing system and the result of authentication of the biometric data. For example, additional biometric data may comprise fingerprint data, iris scan data, facial recognition data, etc.

In embodiments, the computing device is further adapted to: process the brain activity signal prior to providing the brain activity signal to the authentication service computing device. For example, the data (brain activity signal and/or reference data) may be normalized, standardized, averaged, its dimensionality reduced, etc., or combinations thereof.

According to a third aspect of the disclosure there is provided an authentication service computing device comprising at least one processor and at least one memory. The authentication service computing device is adapted to receive a captured brain activity signal from a computing device associated with a user; compare the brain activity signal with reference data; and determine, based at least in part on the comparison, whether the identity of the user can be confirmed. In embodiments, the computing device associated with a user is a user device, such as a personal computer, laptop, mobile device, such as a tablet or mobile phone, etc. In other embodiments, the computing device associated with a user is a computing device provided by a third party and used by a user to authenticate themselves, for example, a cash machine, point of sale terminal, etc.

In embodiments, the authentication service computing device is further adapted to communicate the result of the comparison to the computing device associated with the user.

In embodiments, the authentication service computing device is adapted to receive a captured brain activity signal from a computing device associated with a user, wherein the brain activity signal was captured during or shortly after exposing the user to a stimulus; and compare (i) the brain activity signal in response to the stimulus to (ii) reference data comprising expected brain activity signals in response to the stimulus.

In embodiments, the stimulus may comprise a sensory stimulus. For example, the stimulus may comprise a visual stimulus, an audio stimulus, a haptic stimulus, an olfactory stimulus, or any combinations thereof. Examples of visual stimuli that may be suitable for the present disclosure include: one or more images, one or more videos, and one or more spatial or temporal patterns of light. In some embodiments, the stimulus comprises a rapid succession of sensory stimuli.

In embodiments, the authentication service computing device is adapted to receive a captured brain activity signal from a computing device associated with a user, wherein the brain activity signal was captured while the user is performing a requested action, or shortly thereafter; and compare (i) the captured brain activity signal to (ii) reference data comprising expected brain activity signals associated with an authentic user performing the requested action. In some such embodiments, the requested action may be to enter a PIN, password or other secret identifier, or to select images displayed on a screen.

In embodiments, the authentication service computing device is adapted to receive a captured brain activity signal from a computing device associated with a user, wherein the brain activity signal was captured while the user is entering a secret identifier at a computing device, or shortly thereafter; and compare the captured brain activity signal with reference data comprising (i) expected brain activity signals associated with users entering secret information that they enter routinely and (ii) expected brain activity signals associated with users entering secret information that they do not enter routinely.

In embodiments, the authentication service computing device is adapted to receive a captured brain activity signal from a computing device associated with a user, wherein the brain activity signal was captured while the user is selecting images displayed on a screen or shortly thereafter; and compare the captured brain activity signal to reference data comprising expected brain activity signals associated with the user when selecting those particular images.

In embodiments, the reference data is selected from: data uniquely associated with the user, data associated with a cohort of individuals, theoretical data, and combinations thereof.

In embodiments, the authentication service computing device is adapted to receive a captured brain activity signal from a computing device associated with a user, wherein the brain activity signal was captured while the user is requested to think a predetermined thought, or shortly thereafter; and compare (i) the captured brain activity signal to (ii) reference data comprising expected brain activity signals associated with the user thinking the particular thought.

In embodiments, the brain activity signal is an electroencephalograph or a magnetoencephalograph. In embodiments, the brain activity signal comprises measurements of the electrical potential at one or more locations on a user's scalp. In embodiments, the measurement locations are positioned according to the International 10/20 system.

In embodiments, the authentication service computing device is adapted to: receive a captured brain activity signal from a computing device associated with a user and a PIN, password or other secret identifier captured from the user (for example, by requesting the user to provide a PIN, password or other secret identifier); authenticate the PIN, password or secret identifier; and determine based at least in part on the comparison between the brain activity signal and reference data, and at least in part on the result of the authentication of the PIN, password or secret identifier, whether the identity of the user can be confirmed.

In embodiments, the authentication service computing device is adapted to: receive a captured brain activity signal from a computing device associated with a user and additional biometric date captured from the user (for example, comprising fingerprint data, iris scan data, facial recognition data, etc.); authenticate the biometric data; and determine based at least in part on the comparison between the brain activity signal and reference data, and at least in part on the result of the authentication of the biometric data, whether the identity of the user can be confirmed.

In embodiments, the authentication service computing device is further adapted to: process the brain activity signal prior to comparing it with reference data. For example, the data (brain activity signal and/or reference data) may be normalized, standardized, averaged, its dimensionality reduced, etc., or combinations thereof.

According to a fourth aspect of the disclosure, a computing device adapted for authentication of a user is provided, comprising at least one processor and at least one memory. The computing device is adapted to: communicate with a brain activity sensing system to capture a brain activity signal from the user; compare the captured brain activity signal with reference data; and determine based at least in part on the comparison, whether the identity of the user can be confirmed.

Any of the features described in relation to the computing device and authentication service computing device of the second and third aspects may be present in embodiments of this aspect of the disclosure.

According to yet a further aspect. a system for authentication of a user is provided, the system comprising the computing device of the second or fourth aspects above, and a brain activity sensing system.

In embodiments, the brain activity sensing system comprises an electroencephalogram.

Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible. The applicant reserves the right to change any originally filed claim or file any new claim accordingly, including the right to amend any originally filed claim to depend from and/or incorporate any feature of any other claim although not originally claimed in that manner.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure. One or more embodiments of the disclosure will now be described, by way of example only, with reference to the accompanying drawings, in which.

Figure 1:
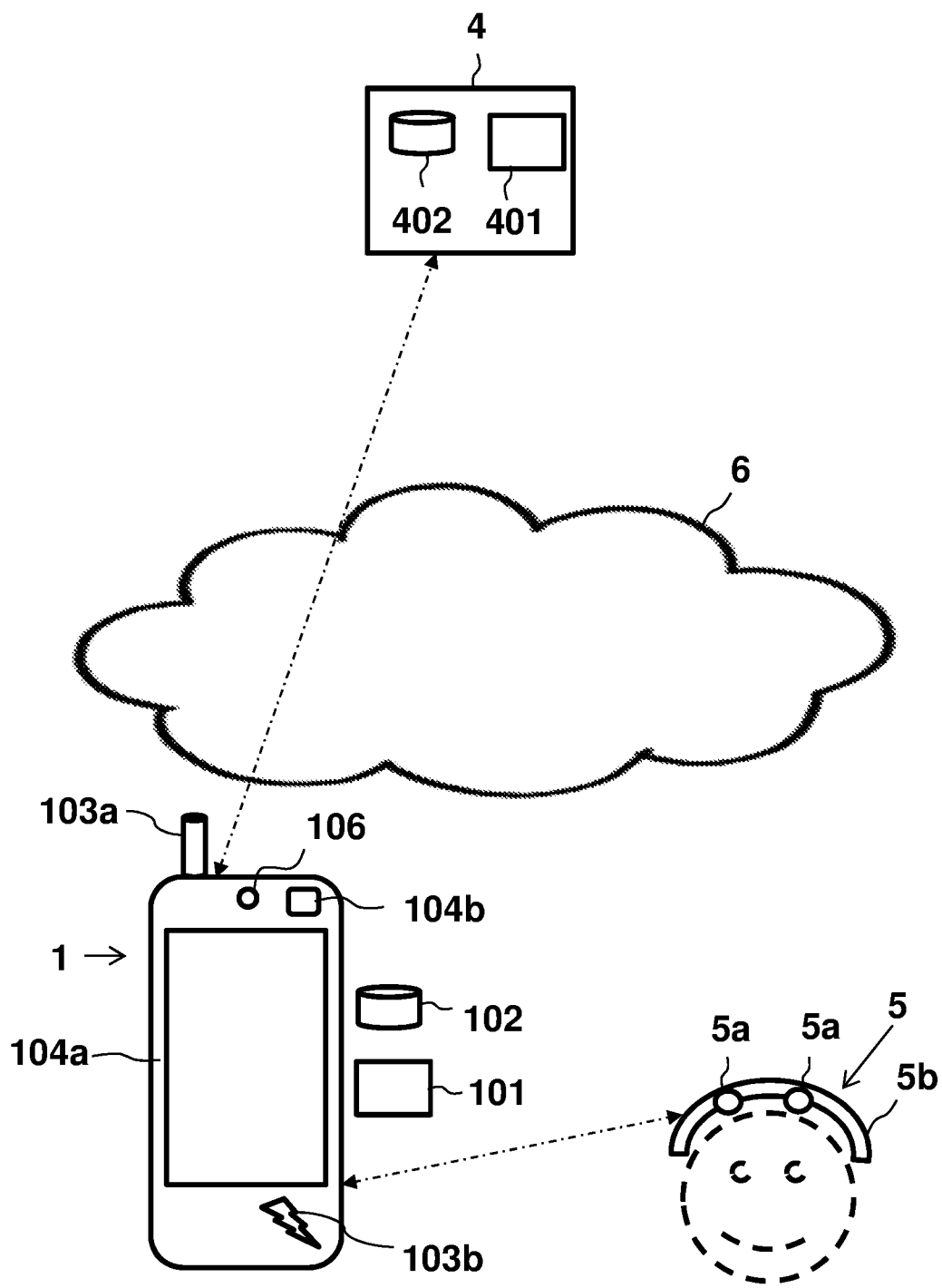
FIG. 1 shows an exemplary computing system in which embodiments of the present disclosure may be used.

Where the figures laid out herein illustrate embodiments of the present disclosure, these should not be construed as limiting to the scope of the disclosure. Where appropriate, like reference numerals will be used in different figures to relate to the same structural features of the illustrated embodiments.

DETAILED DESCRIPTION

Embodiments will be described, by way of example only, with reference to the drawings. The description and specific examples included herein are intended for purposes of illustration only and are not intended to limit the scope of the present disclosure. Specific embodiments of the disclosure will be described below with reference to the Figures.

FIG. 1 shows an exemplary computing system in which embodiments of the present disclosure may be used.

The approach taken to authenticating a user is applicable to any form of computing device, but it has particular utility for mobile computing devices, such as smart phones, and relevance to applications, such as mobile banking. Given this relevance, FIG. 1 shows the relevant physical elements of a computing system comprising a computing device 1 in the form of a mobile computing device, such as a smart phone. However, as the skilled person would understand, the methods of the disclosure are applicable to other computing devices (such as, e.g., a tablet, laptop computer, fixed computing device, such as a personal computer, ATM, point-of-sale terminal, security system, e.g., for a safe, locked door or gate, etc.) and other situations where authentication is desirable, such as, e.g., electronic communications including electronic mail, online banking, logging into a user computing device (e.g. personal computer, phone, tablet, etc.), entering a secured facility, or making payments.

The computing device 1 has at least one processor 101 and at least one memory 102 together providing at least one execution environment. Typically, a mobile device has firmware and applications run in at least one regular execution environment (REE) with an operating system, such as iOS, Android or Windows. The computing device 1 may also be equipped with means 103 to communicate with other elements of a computing infrastructure. These may comprise a wireless telecommunications apparatus 103*a* for communication with a wireless telecommunications network and local wireless communication apparatus 103*b*.

The computing device 1 comprises a user interface 104 which includes at least a display 104*a*. The display 104*a* may be a touch screen. Other types of user interfaces may be provided, such as e.g. a speaker 104*b*, keyboard, one or more buttons (not shown), etc. Further, the computing device 1 may be equipped with data capture means 106, such as a camera, or a microphone.

An authentication service computing system 4 is also shown in FIG. 1. The computing device 1 can be connected to the authentication service computing system 4 by a network connection, such as via the public internet 6. The authentication service computing system 4 typically comprises one or more processors 401 (e.g., servers), a plurality of switches (not shown), and one or more databases 402, and is not described further here as the details of the authentication service computing system 4 used are not necessary for understanding how embodiments of the disclosure function and may be implemented. As the skilled person will understand, in some embodiments, some or all of the functions of the authentication service computing system 4 may be performed by the computing device 1. As such, in embodiments the authentication service computing system 4 may be omitted entirely.

A brain activity sensing system 5 is also provided. The brain activity sensing system 5 may be wirelessly connected to the computing device 1, for example via local communication protocols such as Bluetooth, or via the internet 6. Alternatively, the brain activity sensing system 5 may be connected to the computing device 1 via a wired connection. In embodiments, the brain activity sensing system 5 may instead or in addition be connected to the authentication service computing system 4.

In embodiments, the brain activity sensing system 5 comprises one or more sensors 5a that are configured to detect a brain activity signal (also referred to herein as "brain activity data") from a user. In embodiments, the one or more sensors 5a are electrodes (such as e.g. contact or non-contact electrodes, dry active electrodes, wet active electrodes, etc.), and the brain activity sensing system 5 is configured to capture brain activity signals in the form of encephalographs. In other embodiments, the brain activity sensing system 5 is configured to capture brain activity signals in the form of magnetoencephalographs.

In embodiments, the brain activity sensing system 5 comprises a processor (not shown) which is configured to communicate the signals from the sensors 5a to a computing device to which the brain activity sensing system 5 is connected, such as the computing device 1. The processor of the brain activity sensing system 5 may also be configured to pre-process the signals before communicating them to the computing device 1.

In embodiments, the brain activity sensing system 5 comprises a headset 5b, or any type of headgear (such as, e.g., a headband, cap, helmet, hat, etc.) configured to support the sensors 5b and locate them in a sensing position relative to the brain of the user. For example, the sensors 5a may be configured to measure an electrical signal (e.g., the electrical potential) at one or more locations on a user's scalp, and the headgear 5b may be configured such that the sensors acquire measurements at locations positioned according to the International 10/20 system, when the headgear 5b is donned by the user.

In embodiments, the brain activity sensing system 5 comprises sensors configured to measure electrical signals indicative of neurological activity through skin and/or mucosa of any part of the human body where such activity can be detected. In embodiments, the brain activity sensing system 5 comprises sensors configured to measure electrical signals indicative of neurological activity directly in the brain or nerve fibre, for example through implanted electrodes.

The brain activity sensing system 5 is not described further here as the details of the brain activity sensing system 5 used are not necessary for understanding how embodiments of the disclosure function and may be implemented. Further, brain activity sensing systems 5 suitable for use in the context of the disclosure are known from, e.g., US 2008/0177197, WO 2015/017563 (amongst others) and commercial brain activity sensing systems are available.

Figure 2:
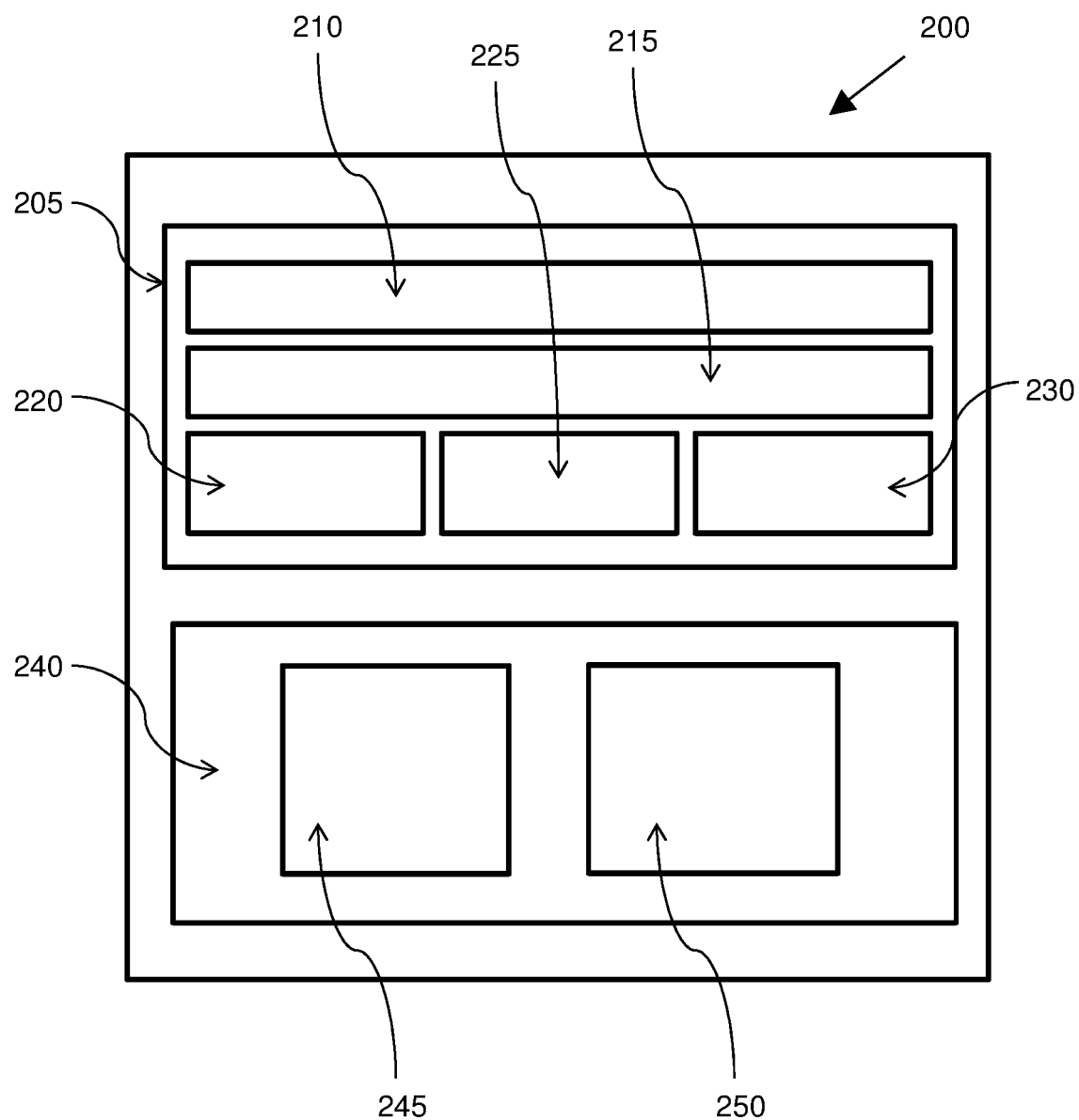
FIG. 2 illustrates schematically the software architecture of a computing device, in accordance with an embodiment of the disclosure.

FIG. 2 illustrates the software architecture of a mobile computing device 200 which can be used as computing device 1, in accordance with an embodiment of the disclosure. In FIG. 2, a main operating environment 205 of the mobile computing device 1 is shown along with a protected operating environment 240. The protected operating environment 240 may be a SIM (not shown). Alternatively, there may be a sandbox or other logically protected environment in the main operating environment to provide a secure environment.

The main operating environment 205 comprises an application processor 210 and associated memories 215. The main operating environment 205 also comprises other applications normally needed by such a mobile computing device, such as a browser 220, a modem 225, and data capture means drivers 230 (e.g., a camera driver).

The protected operating environment 240 may comprise a biometric application 245 and an application that uses the biometric application 245 for user authentication purposes. In this case, the application is a transaction application, specifically a mobile payment application 250, whereby the biometric application 245 is called by the mobile payment application 250. In FIG. 2, both applications are explicitly shown in the protected operating environment. The applications may be located within the SIM or within another physically or logically protected environment so that third parties can have confidence in biometric results produced by the biometric application 245. Alternatively, some parts of the biometric application 245 and the mobile payment application 250 may be situated in the protected operating environment. Further, data from one or both of these applications may be located in a protected memory.

The biometric application 245 communicates with (i.e., contains instructions that, when executed by the processor 210, cause the mobile device 200 to communicate with) at least the brain sensing system 5 to obtain brain activity signals. In embodiments, the biometric application 245 communicates with other applications, such as, e.g., one or more of the data capture means drivers 230, to obtain additional biometric signals, such as a voice recording from a microphone driver, a picture of a user's face or fingerprint from a camera driver, etc. In embodiments, the biometric application 245 processes the brain activity signals received from the brain sensing system 5. In embodiments, as will be further explained below, the biometric application 245 may also communicate with the authentication service computing system 4 to send brain activity signals in raw or processed form, or combinations of brain activity signals and other biometric signals in raw or processed form, to the authentication service computing system 4.

Figure 3:
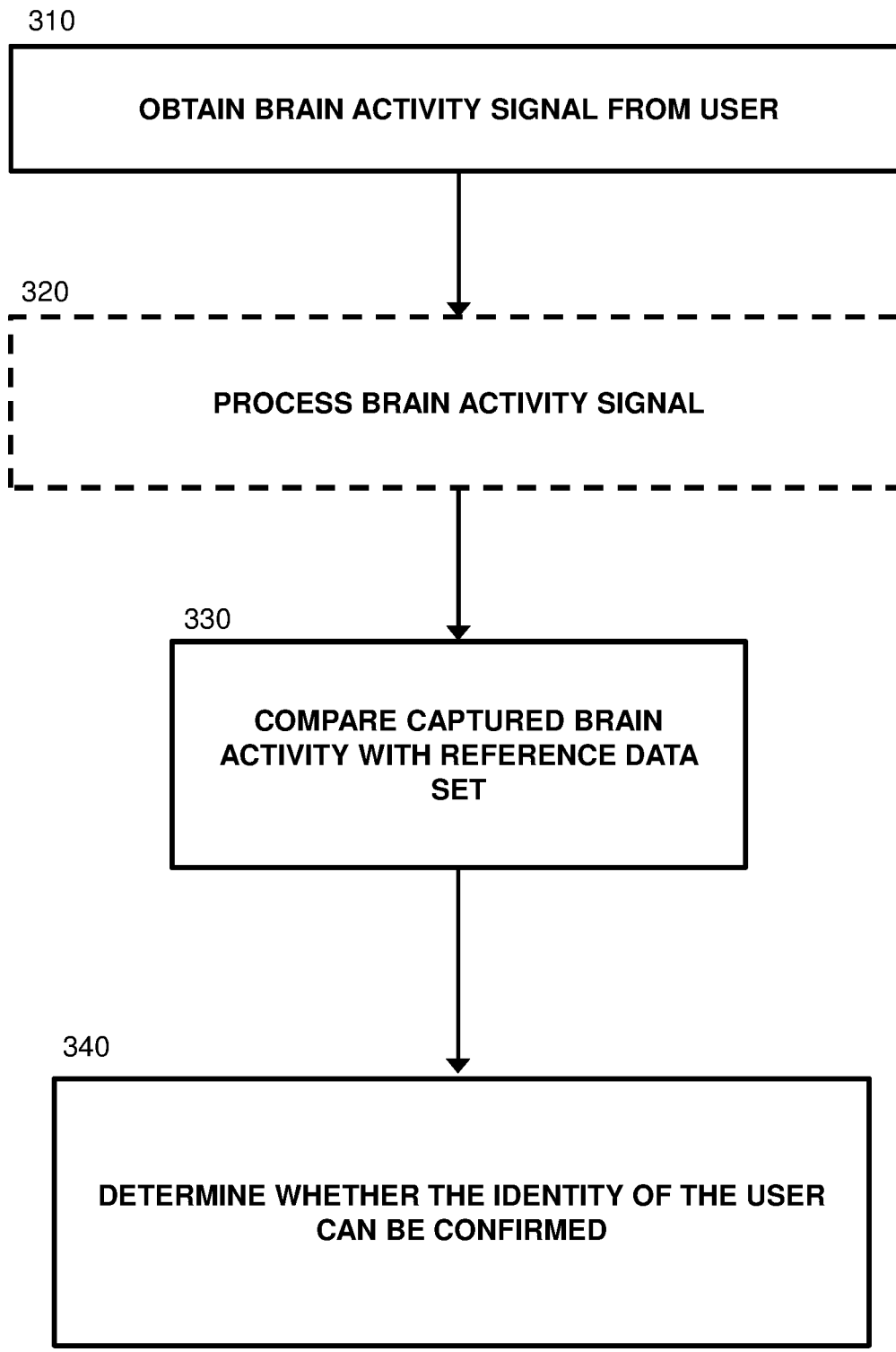
FIG. 3 is a flow chart illustrating the general process of authenticating a user, according to an embodiment of the present disclosure.

FIG. 3 shows a general embodiment of a method of authentication of a user using brain-activity signals.

First of all, a brain activity signal is captured, at step 310, from a user. Optionally, the brain activity signal may be processed, at step 320. Any data processing approaches known in the art may be used, including noise reduction approaches, dimensionality reduction (e.g., PCA, ICA, etc.), averaging, filtering, normalising, etc. This is followed by comparing, at step 330, of the captured brain activity signal with a reference data set. Then, at step 340, it is determined, based at least partially on the comparison of step 330, whether the identity of the user can be confirmed.

In embodiments, the reference data comprises data uniquely associated with the user. For example, data uniquely associated with the user may form a learning dataset which is acquired from the user in a set up phase. For example, a learning dataset may be acquired in a set up phase in a similar way as users are already familiar with fingerprint authentication on mobile devices, whereby fingerprint authentication is enabled following acquisition of fingerprint data upon repeated application of a finger on the fingerprint reader. Optionally, the learning data set may be complemented with new data acquired through use of the system by the user. As such, the learning dataset may be continuously updated to improve the accuracy of the determination, at step 340. As will be explained further below in relation to reference data comprising data associated with a cohort of individuals, metadata associated with the samples in the learning dataset may enable the learning data to be classified into different categories to derive information about brain activity patterns in different situations, which are uniquely associated with the user.

In embodiments, the reference data comprises data associated with a cohort of individuals. For example, data may be acquired from a cohort of users, non-users, or combinations thereof. Such may form a learning dataset from which general trends may be extracted, and new data acquired from a user during an authentication process can be compared to these general trends. Such general trends may be associated with one or more of: confidence levels, metadata associated with the individuals in the cohort, metadata associated with individual data samples in the reference data, etc., in order to increase the accuracy of the comparison.

Optionally, the learning data set may be complemented with new data acquired through use of the system by the user to be authenticated, or all users of the system. As such, the learning dataset may be continuously updated to improve the accuracy of the determination, at step 340. As the skilled person would understand, continuous updating of the learning dataset may increase the statistical power of any test applied on the data (such as, e.g., the comparison between a brain activity signal from a user and the learning data, or any conclusion regarding general trends in the data). Further, complementing the learning data set with new data acquired through use of the system by the user to be authenticated may enable the learning data set to be tailored to the user to be authenticated. Data associated with a cohort of individuals may be used to classify a brain activity signal according to metadata associated with the individuals, such as, e.g., age, gender, etc. Such classification may be compared with the expected classification associated with a user to be authenticated.

Further, data associated with a cohort of individuals may be used to classify a brain activity signal according to metadata associated with the samples in the reference data. For example, the metadata associated with samples in the reference data may enable the data to be separated into brain activity signals obtained from individuals when exposed to information that the individuals are recollecting, as opposed to information that is not expected to trigger a recollection. For example, different brain activity signals may be obtained when individuals are looking at images that they are familiar with, rather than images that they are not familiar with. Images that an individual is familiar with may include pictures of people that the individual knows well, pictures that the individual has recently uploaded, liked or otherwise encountered on social media or other browsing activity, pictures that the individual has previously designated, patterns or characters that embody an individual's chosen PIN or password, etc. As another example, different brain activity signals may be obtained when individuals are hearing sounds that they are familiar with, rather than sounds that they are not familiar with. Sounds that an individual is familiar with may include the voice of people that the individual knows well, songs or extracts of songs that the individual has recently listened to, sounds that the individual has previously designated, etc.

As another example, the metadata associated with samples in the reference data may enable the data to be separated into brain activity signals obtained from individuals while performing a routine action (e.g. entering a password or PIN that the individual has entered countless times in the past), as opposed to performing an action that requires concentration.

As a further example, the metadata associated with samples in the reference data may enable the data to be separated into brain activity signals obtained from individuals in different emotional states. For example, individuals may be in different emotional states when providing their own credentials and when providing someone else's credentials.

In embodiments, the reference data comprises theoretical data. For example, the reference data may embody knowledge about expected patterns of brain activity in a user when exposed to information that the user is recollecting, as explained above. The reference data may instead, or in addition, embody knowledge about expected patterns of brain activity in a user when the user is performing a routine action (e.g., entering a password or PIN that the user has entered countless times in the past) as opposed to an action that requires concentration (e.g., remembering a PIN or password that has recently come to be known to the user). Further, the reference data may instead, or in addition, embody knowledge about expected patterns of brain activity in a user as a function of their emotional state, as explained above.

Methods of analysing brain activity data in the form of, e.g., electroencephalographs (EEG) are known in the art and will not be discussed further herein. For example, methods for classifying mental states based on EEGs are disclosed in, e.g., US 2007/0060831.

In embodiments, the reference data is stored in the database 402 of the authentication service computing system 4. In such embodiments, step 330 and optionally step 340 may be performed by the authentication service computing system 4. In embodiments, the authentication service computing system 4 may compute the comparison at step 330, and return the result to the computing device 1 to make the decision of step 340. Alternatively, the authentication service computing system 4 may make the decision of step 340, and return the result to the computing device 1. In other embodiments, the reference data is stored locally on the computing device 1, such as in memory 102. In such embodiments, steps 330 and 340 may be performed by the computing device 1.

In embodiments, determining whether the identity of the user can be confirmed at step 340 comprises calculating a score for the comparison of step 330. Depending on the type of reference data that is used and the type of comparison that is made, a score may represent a level of statistical confidence in the result of the comparison. For example, the comparison can comprise classification of the brain activity signal from the user based on a learning dataset (which as explained above can be separated for example into categories which represent expected patterns of brain activity, whether empirical or theoretical, when a user is performing a routine action vs. performing an action that requires concentration; when a user is in an emotional state associated with provision of the user's own credentials vs. an emotional state associated with provision of someone else's credentials; etc.) and the score can represent a level of certainty in the assigned class, a goodness of fit/similarity with an expected signal representative of the class, etc. As another example, the comparison can comprise a comparison with a training set associated with the user and the score may comprise a metric of similarity with the training set.

In embodiments, the determination, at step 340, may comprise calculation of the score (if the score is not inherent to the comparison step, e.g., if the score is a measure of statistical confidence associated with the result of the comparison, as opposed to a quantification of the comparison itself, e.g., a metric of similarity). In embodiments, the determination, at step 340, comprises the comparison of the score previously obtained against a threshold value. Depending on the nature of the score, the comparison may result in a positive authentication of the user if the score is below a threshold (for example, if the score is a p-value) or above the threshold (for example, if the score is a metric of similarity).

In embodiments, at step 340, the determination of whether the identity of the user can be confirmed is based on additional information besides the comparison of step 330. In embodiments, the determination, at step 340, of whether the identity of the user can be confirmed may require one or more additional comparisons and/or authentications to be positive. For example, the determination, at step 340, may comprise authentication of a PIN or password entered by the user at the computing device 1. The determination, at step 340, may also comprise the capture of additional data, for example, biometric data, and the comparison of this data with associated reference data. For example, authentication of the user, at step 340, may require a positive result of the comparison of step 330 and a positive authentication of any of the user's fingerprint, voice print, iris scan, facial recognition, etc. Processes for authentication via other such biometrics are known in the art and will not be discussed further. As another example, biometric data indicative of the emotional state of the user may be collected and used in the determination, at step 340. For example, data, such as heartbeat, eye movement, etc., may be used. Such data may be acquired by the computing device 1, for example, by communicating with a health tracker or other smart device.

In embodiments discussed in more detail below, the interpretation of the captured brain activity data and its use for authentication will be carried out in a server remote from the user's mobile phone, i.e., by the authentication service computing system 4. In embodiments, however, this process may be carried out in whole or in part on the computing device 1 (e.g., user's mobile phone), preferably in such a way that a third party can have confidence in the authentication result (with relevant processes or data secured or appropriately protected). In the approach discussed below, however, the comparison process and the authentication result are achieved remotely, with an authentication result transmitted back to the user computing device and/or to any other system element that should receive this information, depending on the reason why authentication is required.

Different approaches to providing an authentication process according to embodiments of the disclosure will now be discussed below with references to FIGS. 4 to 6. These differ primarily in how the biometric samples for comparison are obtained, and how the authentication process is carried out.

Figure 4:
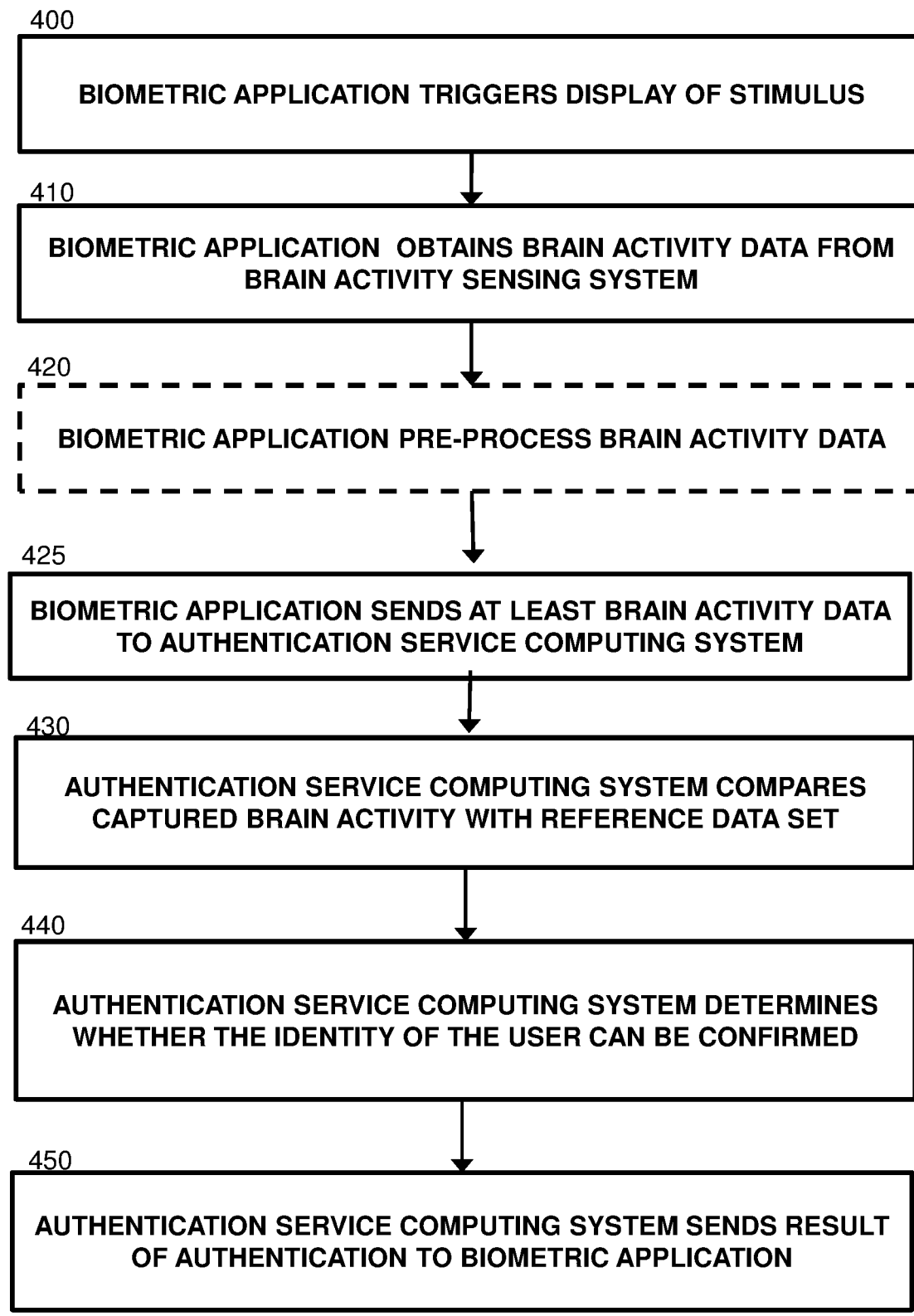
FIG. 4 illustrates schematically method steps in a first embodiment of the disclosure.

FIG. 4 illustrates schematically method steps in a first embodiment of the disclosure.

The first step is for the biometric application 245 to trigger the generation of a stimulus. For example, a stimulus may be any sensory stimulus, such as a visual, haptic, audio or olfactory stimulus. Conveniently, as shown on FIG. 4, the stimulus may be a visual stimulus displayed 400 on the display 104*a* of the computing device 1.

In embodiments, the stimulus comprises a rapid succession of sensory stimuli. Advantageously, such stimuli may be able to trigger brain activity that is associated with involuntary reactions that are faster than conscious recollection. As such, a user may not have a conscious recollection of the stimuli that have been provided.

In embodiments, the stimulus comprises a rapid succession of images, some of which are expected to trigger a reaction in the user, and some of which are not. For example, the stimulus may comprise images showing random character strings and images showing character strings that the user is expected to recognize, such as the user's password, PIN etc. Advantageously, displaying the images in rapid succession minimizes the risk that a user would be able to consciously recollect any of the character strings shown, for example, to learn the password or PIN. In other examples, the stimulus may comprise images of people that the user knows and images that the user is not expected to know. Images of people that the user knows may be selected by the user themselves in a set-up phase, or may be automatically generated, for example, using social media or contact data. In embodiments, the stimulus may comprise images that the user is expected to recognize because (s)he has recently encountered them. Such images may be derived, for example, from browsing history, social media, GPS data, etc. Similarly, sounds may be used instead of images in the embodiments described above. For example, rapid succession of sound samples may be used instead of images. Further, sounds may comprise voice recordings of people that the user is expected to recognize, and voice recordings of people that the user is not expected to recognize. Alternatively, sounds may comprise sounds that the user has recently encountered.

As such, in embodiments, the biometric application 245 may communicate with other applications on the computing device 1 to obtain the stimuli. Alternatively, the biometric application 245 may communicate with the authentication service computing system 4 to obtain the stimuli, and may simply cause the stimuli received from the authentication service computing system 4 to be produced by the computing device 1.

A step 410, the biometric application 245 communicates with the brain activity sensing system 5 to capture a brain activity signal from a user while the user is being exposed to the stimulus and/or shortly thereafter. Optionally, the brain activity signal may be pre-processed, at step 420, by the biometric application 245. For example, dimensionality reduction, compression, filtering or any other data processing technique may be applied to the brain activity data. At step 425, the biometric application 245 sends the brain activity data to the authentication service computing system 4. Optionally, the biometric application 245 may additionally send information about the stimulus to the authentication service computing system 4. For example, the biometric application 245 may send information about the sequence of stimuli comprised in the stimulus to the authentication service computing system 4, or any other information that may allow the authentication service computing system 4 to determine the characteristics of the stimulus that would impact the brain activity of the user exposed to the stimulus. As previously mentioned, in embodiments, the biometric application 245 may acquire and send additional biometric data to authentication service computing system 4, which may be used as further authentication means. At step 430, the authentication service computing system 4 compares the brain activity data with a reference data set, as explained above. For example, the comparison may aim to determine whether the brain activity data is as expected for any user or this particular user in response to this particular stimulus. In particular, identifiably different brain activity may be expected when a user is viewing an image showing a person they know, as opposed to a person they do not know. At step 440 the authentication service computing system 4 determines, based at least partially on the comparison of step 430, whether the identity of the user can be confirmed. At step 450, the authentication service computing system 4 sends the result of the comparison to the biometric application 245. Optionally, the biometric application 245 may communicate the result of the authentication to any application that requested it, such as, for example, a mobile banking application. Alternatively, the authentication service computing system 4 may directly communicate the results of the authentication to the application/computing device that requires it. In embodiments, step 440 may be performed by the biometric application 245 on the computing device 1. In such embodiments, steps 440 and 450 may be reversed, and at step 450 the authentication service computing system 4 may send the result of the comparison step 430 instead of the result of the determination step 440.

Figure 5:
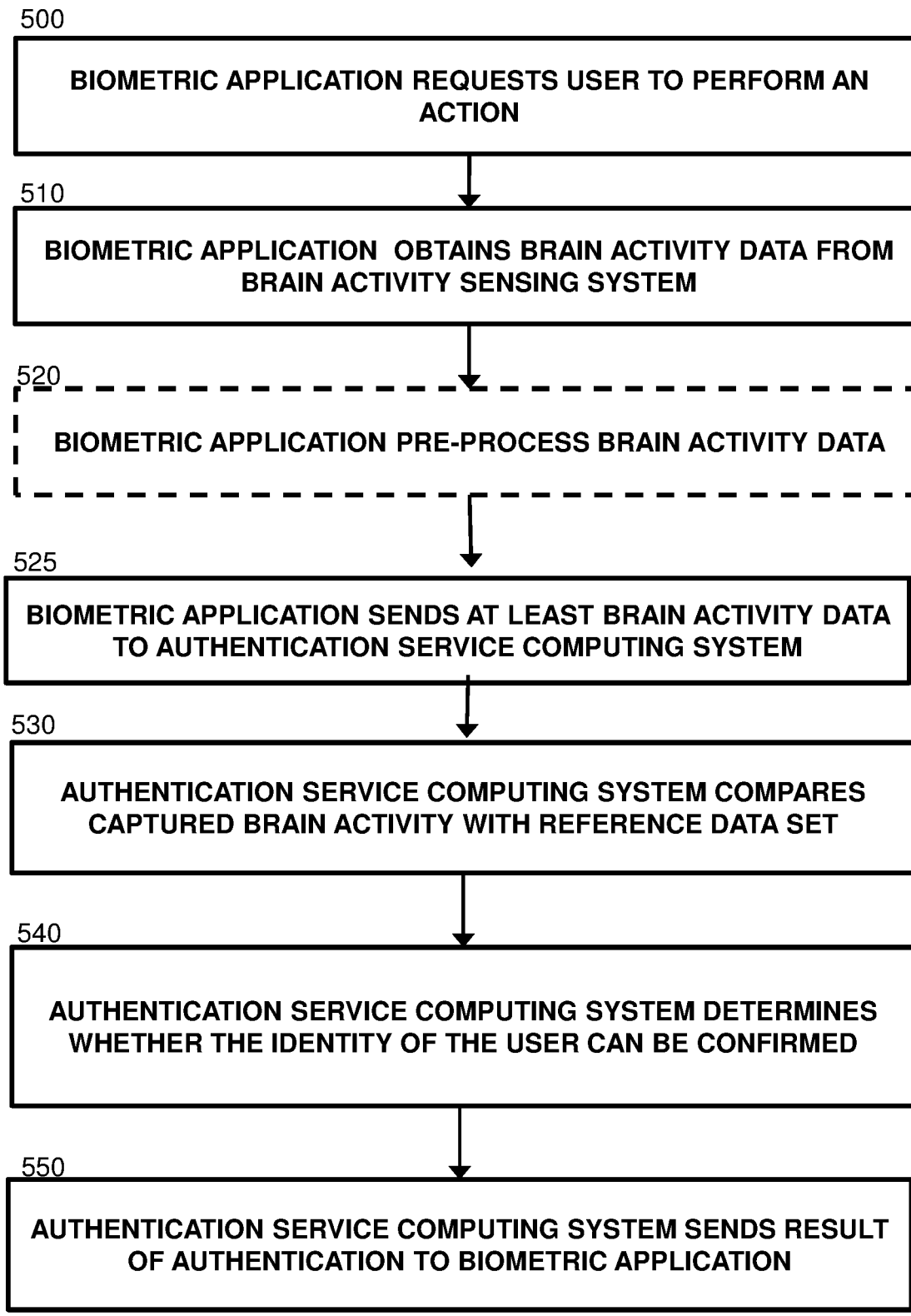
FIG. 5 illustrates schematically method steps in a second embodiment of the disclosure.

FIG. 5 illustrates schematically method steps in a second embodiment of the disclosure.

The first step is for the biometric application 245 to request, at step 500, the user to perform an action. For example, the biometric application 245 may request the user to enter (e.g., type, speak or otherwise provide) a PIN, a password, a pattern, etc. As another example, the biometric application 245 may request the user to select images displayed on a device.

A step 510, the biometric application 245 communicates with the brain activity sensing system 5 to capture a brain activity signal from a user while the user is performing the action and/or shortly thereafter. Optionally, the brain activity signal may be pre-processed, at step 520, by the biometric application 245, as explained above. At step 525, the biometric application 245 sends the brain activity data to the authentication service computing system 4. Optionally, the biometric application 245 may additionally send information about the action to the authentication service computing system 4. For example, the biometric application 245 may send information about whether the action performed by the user was as expected (e.g., the correct PIN or password was entered), whether it was performed slower or faster than the user would on average perform the action, what the action requested was, etc. As previously mentioned, in embodiments, the biometric application 245 may acquire and send additional biometric data to authentication service computing system 4, which may be used as further authentication means. At step 530, the authentication service computing system 4 compares the brain activity data with a reference data set, as explained above. At step 540 the authentication service computing system 4 determines, based at least partially on the comparison of step 530, whether the identity of the user can be confirmed. For example, the comparison may aim to determine whether the brain activity data is as expected for any user or this particular user when performing this particular action. In particular, identifiably different brain activity may be expected when a user is entering a password or PIN that is familiar to them compared to a password of PIN that is not familiar. As another example, a particular user may have an identifiable pattern of brain activity when performing certain actions. For example, certain combinations of words being entered by a user may trigger a particular combination of emotional states that can be attributable to the user. Similarly, active selection of certain items/images on a screen may trigger particular brain activity in a specific user that may not be observed in another user when exposed to the same combination of images, even if the user did select the same images.

At step 550, the authentication service computing system 4 sends the result of the comparison to the biometric application 245. Optionally, the biometric application 245 may communicate the result of the authentication to any application that requested it, such as, for example, a mobile banking application. Alternatively, the authentication service commuting system 4 may directly communicate the results of the authentication to the application/computing device that requires it. In embodiments, step 540 may be performed by the biometric application 245 on the computing device 1. In such embodiments, steps 540 and 550 may be reversed, and at step 550 the authentication service computing system 4 may send the result of the comparison step 530 instead of the result of the determination step 540.

Figure 6:
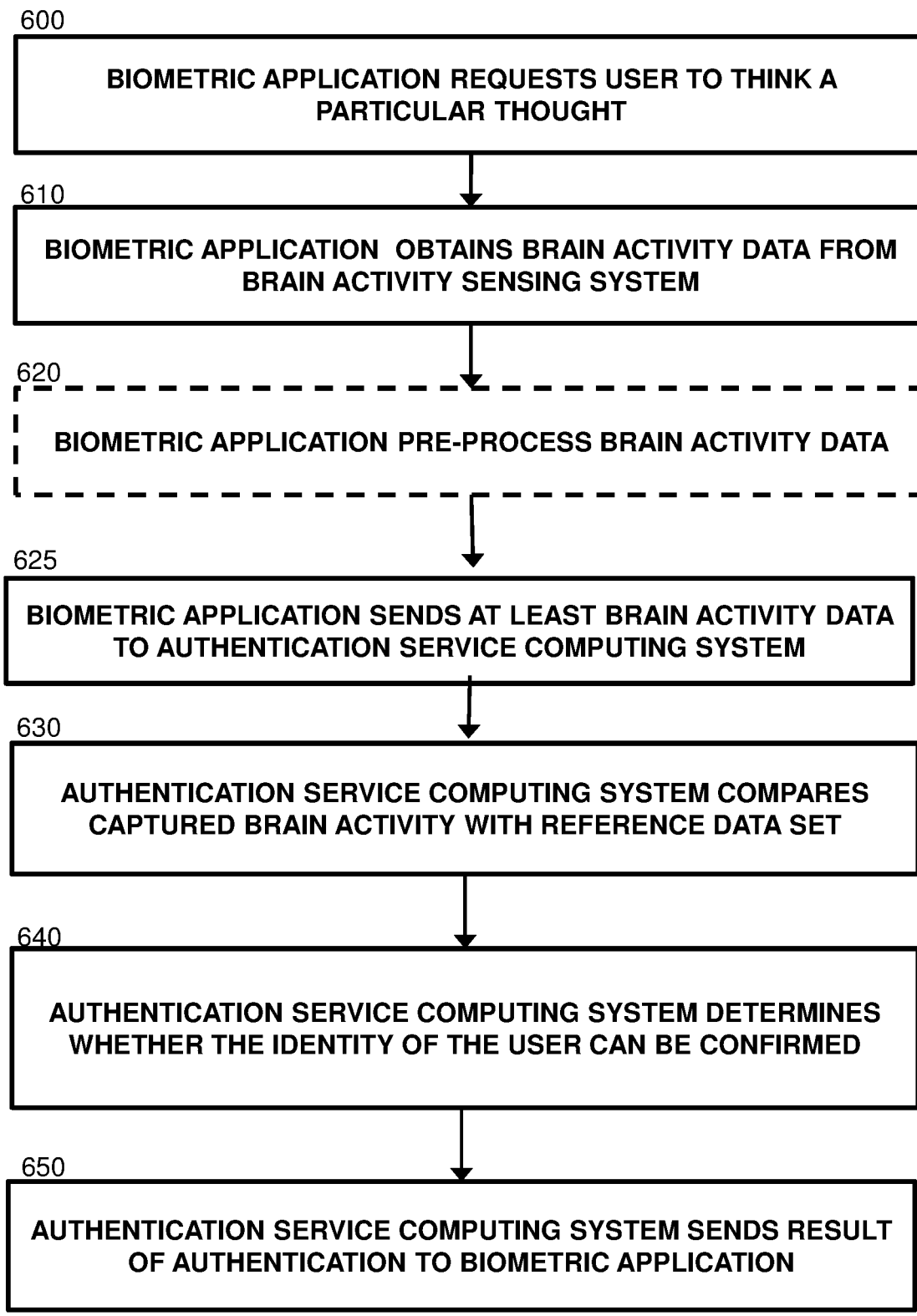
FIG. 6 illustrates schematically method steps in a further embodiment of the disclosure.

FIG. 6 illustrates schematically method steps in a third embodiment of the disclosure.

The first step is for the biometric application to request the user to think a predetermined thought.

The first step is for the biometric application 245 to request, at step 600, the user to think a predetermined thought. In such embodiments, the brain activity pattern associated with the predetermined thought may be recorded in the reference data in a set up phase. For example, a user may train themselves to think a particular thought, such as think about a particular person, which may put the user in an emotional state that is associated with an identifiable brain activity signal.

A step 610, the biometric application 245 communicates with the brain activity sensing system 5 to capture a brain activity signal from a user while the user is thinking the thought. In such embodiments, it may be possible for the user to cause the biometric application 245 to start and stop recording the brain activity signal. Optionally, the brain activity signal may be pre-processed, at step 620, by the biometric application 245, as explained above. At step 625, the biometric application 245 sends the brain activity data to the authentication service computing system 4. As previously mentioned, in embodiments, the biometric application 245 may acquire and send additional biometric data to authentication service computing system 4, which may be used as further authentication means. At step 630, the authentication service computing system 4 compares the brain activity data with a reference data set, as explained above. At step 640 the authentication service computing system 4 determines, based at least partially on the comparison of step 630, whether the identity of the user can be confirmed. For example, the comparison may aim to determine whether the brain activity data is as expected for the user by comparison with reference data associated with the user.

At step 650, the authentication service computing system 4 sends the result of the comparison to the biometric application 245. Optionally, the biometric application 245 may communicate the result of the authentication to any application that requested it, such as for example a mobile banking application. Alternatively, the authentication service commuting system 4 may directly communicate the results of the authentication to the application/computing device that requires it. In embodiments, step 540 may be performed by the biometric application 245 on the computing device 1. In such embodiments, steps 640 and 650 may be reversed, and at step 650 the authentication service computing system may send the result of the comparison step 630 instead of the result of the determination step 640.

Figure 7:
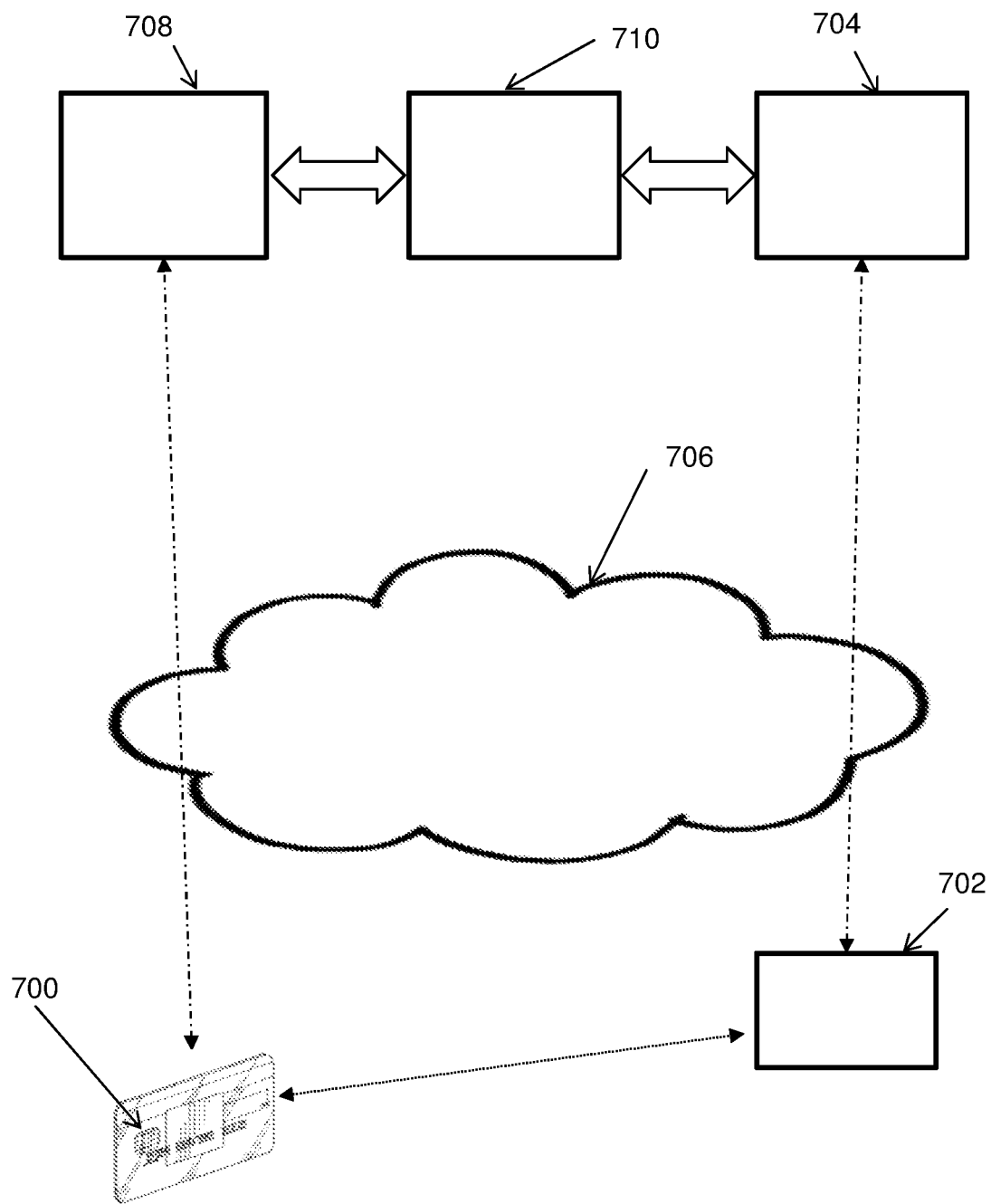
FIG. 7 shows an exemplary transaction infrastructure in which embodiments of the present disclosure may be used.

FIG. 7 shows an exemplary transaction infrastructure in which embodiments of the present disclosure may be used. As previously mentioned, the methods and systems for performing authentication according to the disclosure may advantageously be used as part of a system and method for performing financial transactions. An example of such a system is shown on FIG. 7, where a user is provided with a payment device, in this case a card 700, by an issuer 708. The user can use the payment device 700 to purchase goods or services from a merchant, for example, by interacting with a point of interaction (e.g., a point-of-sale, POS) terminal 702. The merchant POS terminal 702 is connectable to an acquirer 704, either directly or indirectly, preferably in a secure way via a network 706 (either through a dedicated channel or through a secure communication mechanism over a public or insecure channel). The issuer 708 is the bank or any other financial institution that issued the card 700 to the cardholder. The acquirer 704 provides services for card processing to the merchant.

A banking infrastructure 710 connects the issuer 708 and the acquirer 704, allowing transactions to be carried out between them. This banking infrastructure 710 will typically be provided by a transaction card provider who provides transaction card services to the issuer 708. The banking infrastructure 710 enables a merchant associated with one particular bank (acquirer 704) to accept payment transactions from a cardholder associated with a different bank (issuer 708). In particular, as will be further explained below, the banking infrastructure 710 provides authorization at the time of purchase, clearing of the transaction and reconciliation typically within the same working day, and settlement of payments shortly after that. The banking infrastructure 710 comprises a plurality of switches, servers and databases, and is not described further here as the details of the banking infrastructure used are not necessary for understanding how embodiments of the disclosure function and may be implemented.

A typical transaction between the entities in such a system can be divided into two main stages: authorization and settlement. The user initiates a purchase of a good or service from the merchant using their card 700. Details of the card and the transaction are sent by the terminal 702 to the issuer 708 via the acquirer 704 and the banking infrastructure 710 to authorize the transaction. In some cases, for example, if the transaction is considered abnormal by the issuer 708, the cardholder may be required to undergo a verification process to verify their identity and the details of the transaction. Once the verification process is complete the transaction is authorized.

On completion of the transaction between the cardholder and the merchant, the transaction details are submitted by the merchant terminal 702 to the acquirer 704 for settlement. The transaction details are then routed to the relevant issuer 708 by the acquirer 704 via the banking infrastructure 710. Upon receipt of these transaction details, the issuer 708 provides the settlement funds to the banking infrastructure 710, which in turn forwards these funds to the merchant via the acquirer 704. Separately, the issuer 708 and the cardholder settle the payment amount between them.

The authentication methods of the disclosure may advantageously be used in the above system to provide authentication before the transaction is authorized (i.e., as part of the authorization step). In this context, the computing device 1 may also act as the payment device 700. Alternatively, the computing device 1 may also act as the merchant terminal 702. Further, the brain activity sensing system 5 may be provided by either the merchant or the user. In embodiments, the authentication service computing system 4 may be provided by the banking infrastructure 710, or by the issuer 708.

Further embodiments of the disclosure may be provided in accordance with the scope of the disclosure as defined here.

With that said, and as described, it should be appreciated that one or more aspects of the present disclosure transform a general-purpose computing device into a special-purpose computing device (or computer) when configured to perform the functions, methods, and/or processes described herein. In connection therewith, in various embodiments, computer-executable instructions (or code) may be stored in memory of such computing device for execution by a processor to cause the processor to perform one or more of the functions, methods, and/or processes described herein, such that the memory is a physical, tangible, and non-transitory computer readable storage media. Such instructions often improve the efficiencies and/or performance of the processor that is performing one or more of the various operations herein. It should be appreciated that the memory may include a variety of different memories, each implemented in one or more of the operations or processes described herein. What's more, a computing device as used herein may include a single computing device or multiple computing devices.

In addition, and as described, the terminology used herein is for the purpose of describing particular exemplary embodiments only and is not intended to be limiting. As used herein, the singular forms "a," "an," and "the" may be intended to include the plural forms as well, unless the context clearly indicates otherwise. And, again, the terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When a feature is referred to as being "on," "engaged to," "connected to," "coupled to," "associated with," "included with," or "in communication with" another feature, it may be directly on, engaged, connected, coupled, associated, included, or in communication to or with the other feature, or intervening features may be present. As used herein, the term "and/or" and the term "at least one of" includes any and all combinations of one or more of the associated listed items.

Although the terms first, second, third, etc. may be used herein to describe various features, these features should not be limited by these terms. These terms may be only used to distinguish one feature from another. Terms such as "first," "second," and other numerical terms when used herein do not imply a sequence or order unless clearly indicated by the context. Thus, a first feature discussed herein could be termed a second feature without departing from the teachings of the example embodiments.

It is also noted that none of the elements recited in the claims herein are intended to be a means-plus-function element within the meaning of 35 U.S.C. § 112(f) unless an element is expressly recited using the phrase "means for," or in the case of a method claim using the phrases "operation for" or "step for."

Again, the foregoing description of exemplary embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A computing device adapted for authentication of a user through brain activity of the user, the computing device comprising: at least one processor and at least one memory including a protected environment, which is physically or logically protected from an operating system of the computing device, the computing device configured, by a biometric application included in the protected environment of the at least one memory, to:
receive an authentication request from a banking application of the computing device;
direct a user to provide an input, the input including entry of a password or a personal identification number (PIN);
capture the input from the user;
capture, through a brain activity sensing system including a headset and a plurality of sensors, a brain activity signal from the user, while the input from the user is captured;
compare the input from the user to an expected input;
provide the captured brain activity signal and the comparison of the captured input from the user and the expected input to an authentication service computing system;
receive, via the biometric application, from the authentication service computing system, an authentication result indicative of a comparison of the brain activity signal with reference data; and
confirm the identity of the user to the banking application of the computing device, in response to the authentication request, based at least in part on the authentication result from the authentication service computing system and the comparison of the captured input and the expected input.

2. The computing device of claim 1, wherein the computing device is a user device including a personal computer, laptop, or mobile device.

3. A system for authentication of a user, the system comprising the computing device of claim 1, and the brain activity sensing system coupled to the computing device, wherein the plurality of sensors define an electroencephalograph or a magnetoencephalogram.

4. A method of authentication of a user, through brain activity of the user, the method comprising:
receiving an authentication request from a banking application in a mobile computing device;
directing, by a biometric application included in a protected environment of the mobile computing device, a user to provide an input to the computing device, the input including entry of a password or a personal identification number (PIN), the protected environment being physically or logically protected from an operating system of the mobile computing device;
capturing, by the mobile computing device, the input from the user;
capturing, via the biometric application of the mobile computing device, through a brain activity sensing system including a headset and a plurality of sensors, a brain activity signal from the user, while the input is being captured from the user;
comparing, by the biometric application of the mobile computing device, the input from the user to an expected input;
authenticating, via an authentication service computing device, an identity of the user, based on the captured brain activity signal and the comparison of the captured input from the user and the expected input;
receiving, at the biometric application of the mobile computing device, from the authentication service computing device, an authentication result based, in part, on a comparison of the brain activity signal with reference data; and
confirming, by the biometric application of the mobile computing device, the identity of the user to the banking application in the mobile computing device, in response to the authentication request, based at least in part on the authentication result from the authentication service computing device and the comparison of the captured input and the expected input.

5. The method of claim 4, wherein the reference data is selected from: data uniquely associated with the user, data associated with a cohort of individuals, theoretical data, and combinations thereof.

6. The method of claim 4, wherein the brain activity signal is an electroencephalograph or a magnetoencephalograph.

7. The method of claim 4, further comprising:
capturing, via the biometric application of the mobile computing device, additional biometric data associated with the user; and
authenticating the additional biometric data; and
wherein confirming the identity of the user to the banking application is further based on the authentication of the additional biometric data.

8. The method of claim 4, wherein authenticating the identity of the user, based on the captured brain activity signal and the comparison of the captured input from the user and the expected input, includes transmitting, to the authentication service computing device, the captured brain activity signal and information indicative of whether the captured input from the user is consistent with the expected input.

9. The method of claim 8, wherein authenticating the identity of the user, based on the captured brain activity signal and the comparison of the captured input from the user and the expected input, further includes transmitting, to the authentication service computing device, information indicative of a speed of the input relative to an average performance of the action by the user.

* * * * *